United States Patent [19]

Kent

[11] Patent Number: 5,362,442
[45] Date of Patent: Nov. 8, 1994

[54] METHOD FOR STERILIZING PRODUCTS WITH GAMMA RADIATION

[75] Inventor: Randall S. Kent, Thousand Oaks, Calif.

[73] Assignee: 2920913 Canada Inc., Ottawa, Canada

[21] Appl. No.: 95,698

[22] Filed: Jul. 22, 1993

[51] Int. Cl.$^5$ .......................... A61L 2/08; A01N 1/02
[52] U.S. Cl. ........................................ 422/22; 422/44; 250/432 R; 204/158.21; 435/2; 426/240
[58] Field of Search ............... 422/22, 44; 250/432 R, 250/455.11; 204/158.2, 158.21; 426/240, 521; 607/92; 435/2, 236

[56] References Cited

U.S. PATENT DOCUMENTS

| | | | |
|---|---|---|---|
| 2,832,689 | 4/1958 | Proctor | 426/240 |
| 2,920,969 | 1/1960 | Stoddard | 426/240 |
| 2,962,380 | 11/1960 | Wertheim | 99/217 |
| 3,620,944 | 11/1971 | Tanito | 204/158.2 X |
| 4,620,908 | 11/1986 | Van Duzer | 204/158.21 X |
| 4,933,145 | 6/1990 | Uchida et al. | 435/2 X |
| 5,134,295 | 7/1992 | Wälischmiller | 250/455.11 |
| 5,226,065 | 7/1993 | Held et al. | 250/455.11 X |

OTHER PUBLICATIONS

Wyatt, D. E.; Keathley, J. D.; Williams, C. M.; and Broce, B. Is There Life After Irradiation? Part 1, BioPharm Jun. 1993, pp. 34–39.

Wyatt, D. E., Keathley, J. D.; Williams, C. M.; and Broce, B. Is There Life After Irradiation? Part 2, BioPharm Jul.-Aug. 1993, pp. 46–52.

Leitman, S. F. Use of Blood Cell Irradiation in the Prevention of Post transfusion Graft-vs-Host Disease, Transfus. Sci. 1989; 10:219-232.

Martindale's Extra Pharmacopoecia, Glucose p. 1265; prior art.

The Merck Index, Eleventh Edition Glucose pp. 4353-4354, prior art.

Primary Examiner—Robert J. Warden
Assistant Examiner—E. Leigh Dawson
Attorney, Agent, or Firm—Oliff & Berridge

[57] ABSTRACT

A method for sterilizing products to remove biological contaminants such as viruses, bacteria, yeasts, molds, mycoplasmas and parasites is disclosed. The method involves providing the product in a form that contains less than 20% solids and subsequently irradiating the product with gamma irradiation over an extended period of time. Generally the product is irradiated for a period of not less than 10 hours. The extended irradiation time in conjunction with the low level of solids in the product substantially reduces the damage to the product. The method is useful in sterilizing sensitive materials such as blood and blood components.

12 Claims, No Drawings

METHOD FOR STERILIZING PRODUCTS WITH GAMMA RADIATION

FIELD OF THE INVENTION

The present invention relates to a method for sterilizing products to remove biological contaminants such as viruses, bacteria, yeasts, molds, mycoplasmas and parasites.

BACKGROUND OF THE INVENTION

Several products that are prepared for human, veterinary or experimental use may contain unwanted and potentially dangerous contaminants such as viruses, bacteria, yeasts, molds, mycoplasmas and parasites. Consequently, it is of utmost importance that such products are determined to be contaminant free before they are used. This is especially critical when the product is to be administered directly to a patient for example in blood transfusions, organ transplants and other forms of human therapies.

Previously, most procedures have involved methods that screen or test products for a particular contaminant rather than removal of the contaminant from the product. Products that test positive for a contaminant are merely not used. Examples of screening procedures include the testing for a particular virus in human blood from blood donors. However, such procedures are not always reliable. This reduces the value or certainty of the test in view of the consequences associated with a false negative result. False negative results can be life threatening in certain cases, for example in the case of Acquired Immune Deficiency Syndrome (AIDS). Furthermore, in some instances, it can take weeks, if not months, to determine whether or not the product is contaminated.

More recent efforts have focused on methods to remove or inactivate contaminants in the products. Such methods include heat treating, filtration, addition of chemical inactivants and gamma irradiation. It is well documented that gamma irradiation is effective in destroying viruses and bacteria. In fact, one author concludes that gamma irradiation is the most effective method in reducing or eliminating levels of viruses However, when applied to radiation sensitive products, such as blood, gamma irradiation can also have damaging effects on the product itself. In particular, it has been shown that high radiation doses are injurious to red cells, platelets and granulocytes.

SUMMARY OF THE INVENTION

In view of the above, there is a need to provide a method of sterilizing products that is effective in removing biological contaminants while at the same time having no adverse effect on the product. Examples of contaminants include viruses, bacteria, yeasts, molds, mycoplasmas and parasites.

Accordingly, the present invention provides a method for sterilizing a product comprising:
a) providing a product to be sterilized in a form having solid content of less than 20% by weight; and
b) irradiating the product for a period of time of not less than 10 hours at a rate sufficient to provide a total dose of irradiation of between about 20 to about 32 kGy.

By the method of the present invention, the gamma radiation is delivered over an extended period of time which substantially reduces the damage to the product.

Typically, irradiation is carried out for a period of time of not less than 10 hours, preferably from about 20 to about 40 hours, more preferably from about 20 to about 30 hours. The rate of irradiation is in the range of from about 0.5 kGy/hr to about 3.0 kGy/hr, depending on the product to be sterilized as well as the length of the irradiation time. The total amount of irradiation given is typically in the range of from about 20 to about 32 kGy as these levels have been shown to be effective in destroying contaminants such as viruses.

The product is irradiated in a form containing preferably less than 20% solids. Consequently, certain products must be diluted before irradiation. Treating products in diluted form also serves to reduce degradation of the product during irradiation. The choice of diluent depends on the nature of the product to be irradiated. For example, when irradiating blood cells one would choose a physiologically acceptable diluent such as citrate phosphate dextrose.

The process according to the present invention can be carried out at ambient temperature and does not require the cooling, freezing or chemical treatment of the product before the process is carried out. This avoids some of the extra treatment steps that are present in prior art processes.

The method of the present invention is useful in treating organic products that are sensitive to irradiation. Such products may be prone to degradation when irradiated by standard methods. However, irradiating sensitive products by the present method would not be expected to be harmful to the products. The method is typically applied to biological products such as blood and blood components although it is not limited thereto.

In cases where living cells (such as blood cells) are to be irradiated, a scavenger may be added to bind free radicals and other materials that are toxic to cells. A suitable scavenger is ethanol.

The efficacy of the method of the present invention is contrary to what others skilled in this area have predicted. In particular, in U.S. Pat. No. 4,620,908 it is stated that if gamma irradiation was conducted on protein material at ambient temperature, the material would be almost completely destroyed or destroyed to such an extent so as to render the material virtually ineffective. In contrast, when tested on blood, the method of the present invention has not destroyed the viability of the cells contained therein.

DESCRIPTION OF PREFERRED EMBODIMENTS

The following examples ere provided in order to illustrate the method of the present invention and are not meant to limit the scope of the invention.

EXAMPLE 1

Sterilization of Blood

A 200 ml bag of one day old packed red blood cells was used. Ethanol was added to the cells in order to achieve a final ethanol concentration of 0.01%. The red blood cells were diluted by a factor of one in ten using a modified Citrate Phosphate Dextrose (CPD) solution having a pH of about 6.4 to 6.7 and having the following composition in a total volume of 500 ml:

| | |
|---|---|
| Citric Acid Monohydrate | 0.2 g |
| Sodium Citrate Dihydrate | 26.3 g |

| -continued | |
|---|---|
| Sodium Monobasic Phosphate | 2.2 g |
| Sodium Dibasic Phosphate | 1.0 g |
| Dextrose | 3.2 g. |

The cells were irradiated in a commercial size gamma irradiator which contained a cobalt 60 source rack. Irradiation was done off carrier in an unprotected box. The cells were irradiated for twenty four hours at a rate of approximately 1 kGy/hr. After the irradiation period the red blood cells were examined visually and were found to be viable, having a brilliant red colour. A control sample, consisting of packed red blood cells that were not diluted with the above-described CPD solution, was not viable after irradiation.

Four days after the irradiation procedure, the diluted cells were tested for levels of various blood components and the results are shown in Table 1. The control sample consisted of blood from the same bag as the test sample but it did not undergo irradiation. Table 1 illustrates that dilution and irradiation of human blood cells did not significantly alter the white blood cell count. The platelet count and hematocrit values were slightly lower than the control, however these values are still within the range that is seen in normal adult blood. The level of hemoglobin was higher than in the control indicating that some red blood cells did lyse during the procedure. This is also evidenced by the lower red blood cell count. Nevertheless, contrary to what has been previously published, up to 25 kGy of radiation did not destroy the components of blood by the present procedure. The cells were also counted and found to be viable after 25 kGy of gamma irradiation.

TABLE 1

| Component | Irradiated Blood | Control Blood |
|---|---|---|
| White Blood Cells | 4 K/mm$^3$ | 4.8 K/mm$^3$ |
| Red Blood Cells | 3 Mi/mm$^3$ | 7.2 Mi/mm$^3$ |
| Hemoglobin | 42 g/dl | 21 g/dl |
| Hematocrit | 46% | 64% |
| Platelets | 100 k/mm$^3$ | 120 k/mm$^3$ |

EXAMPLE 2

Sterilization of Dextrose

Dextrose (or glucose) containing solutions are used in the treatment of carbohydrate and fluid depletion, in the treatment of hypoglycaemia, as a plasma expander, in renal dialysis and to counteract hepatotoxins. Dextrose is also the preferred source of carbohydrate in parenteral nutrition regimens. In all of the above applications, the dextrose must be sterilized before use. Sterilization of dextrose containing products is generally done by heat sterilization or autoclaving. Unfortunately, these methods have been reported to degrade or caramelize dextrose containing solutions resulting in a color change in the solution. Gamma irradiation of glucose has also been reported to decompose glucose containing solutions. Therefore, there is e need for a method that can sterilize dextrose containing products that does not degrade the product itself. In view of the problems of the prior art, a dextrose solution was treated according to the method of the present invention as follows.

A 5% dextrose solution was irradiated for 24 hours, at a rate of approximately 1 kGy/hr. After irradiation the product was tested and it was found that there was no visible light spectrum change as compared to the non-irradiated control. Therefore, the present method can be useful in sterilizing products that contain dextrose.

While the above two examples relate to two specific embodiments of the method of the present invention, it is to be appreciated that the method can be used to treat an extremely wide variety of products that require sterilization. The fact that the method has proven effective in blood which is a fragile biological material makes it reasonable to predict that the method can be used on many similarly sensitive products. Examples of products that may be treated include pharmaceuticals, proteins, (such as monoclonal antibodies and recombinant DNA products), nucleic acids, blood components, body fluids (such as cerebral spinal fluid, saliva), liposomes, glucose containing products, cell cultures, fetal bovine serum, bone marrow, organs, foods and cosmetics such as shampoos, lotions and creams.

What I claim as my invention is:

1. A method for sterilizing a product comprising:
   a) providing a product to be sterilized in a form having a solid content of less than 20% by weight and
   b) irradiating the product with gamma irradiation for a period of time of not less than 10 hours at a rate sufficient to provide a total dose of irradiation of between about 20 to about 32 kGy.

2. A method according to claim 1 wherein said process is carried out at ambient temperature.

3. A method according to claim 1 wherein said irradiation is provided at a rate of from about 0.5 kGy/hr to about 3.0 kGy/hr.

4. A method according to claim 1 wherein said product is irradiated for a period of time from about 20 to about 40 hours.

5. A method according to claim 1 wherein said product is irradiated for a period of time from about 20 to about 30 hours.

6. A method according to claim 1 wherein said product is an organic product.

7. A method according to claim 1 wherein said product is a biological product.

8. A method according to claim 1 wherein said product is blood or a component thereof.

9. A method according to claim 8 wherein said blood or blood component is first treated with ethanol.

10. A method according to claim 9 wherein said ethanol is in a final concentration of 0.01% and said blood or blood product is diluted before irradiation in a physiologically acceptable diluent to achieve a final dilution of at least 1:10.

11. A method according to claim 10 wherein said physiological acceptable diluent is a modified citrate phosphate dextrose solution having a pH in the range of about 6.4 to about 6.7.

12. A method according to claim 1 wherein said product contains dextrose.

* * * * *